(12) United States Patent
Truckai

(10) Patent No.: US 10,736,491 B2
(45) Date of Patent: Aug. 11, 2020

(54) SURGICAL DEVICE AND METHOD OF USE

(71) Applicant: Corinth MedTech, Inc., Cupertino, CA (US)

(72) Inventor: Csaba Truckai, Saratoga, CA (US)

(73) Assignee: Corinth MedTech, Inc., Cupertino, CA (US)

( * ) Notice: Subject to any disclaimer, the term of this patent is extended or adjusted under 35 U.S.C. 154(b) by 563 days.

(21) Appl. No.: 15/293,604

(22) Filed: Oct. 14, 2016

(65) Prior Publication Data

US 2017/0105607 A1  Apr. 20, 2017

Related U.S. Application Data

(60) Provisional application No. 62/242,519, filed on Oct. 16, 2015.

(51) Int. Cl.
*A61B 1/00* (2006.01)
*A61M 25/01* (2006.01)
(Continued)

(52) U.S. Cl.
CPC .......... *A61B 1/00135* (2013.01); *A61B 1/307* (2013.01); *A61B 17/3421* (2013.01);
(Continued)

(58) Field of Classification Search
CPC . A61B 1/00135; A61B 1/307; A61B 17/3421; A61B 18/1485; A61B 2017/3445; A61B 2017/345; A61B 2019/00982; A61B 2217/005; A61B 2217/007; A61B 2218/002; A61B 2218/007; A61B 1/00131; A61B 1/00147; A61B 1/00151; A61B 1/00154; A61B 1/00163; A61B 1/012; A61B 1/0125; A61B 1/015; A61B 1/018; A61B 1/04; A61B 1/05; A61B 1/053; A61B 1/12; A61B 1/126–147; A61B 1/313; A61B 18/149; A61B 2018/00208;
(Continued)

(56) References Cited

U.S. PATENT DOCUMENTS 7,744,595 B2  6/2010 Truckai et al.
8,221,404 B2  7/2012 Truckai
(Continued)

*Primary Examiner* — Anh Tuan T Nguyen
*Assistant Examiner* — Pamela F Wu
(74) *Attorney, Agent, or Firm* — Wilson Sonsini Goodrich & Rosati

(57) ABSTRACT

A distal end of an introducer sheath into a patient's urethra is advanced into a patient's urethra while flowing an irrigation fluid through a lumen and out a distal end of the introducer sheath into the urethra. The irrigation fluid is simultaneously removed from the urethra through the distal end and lumen of the introducer sheath to establish a circulation of the irrigation fluid in the urethra as the introducer sheath is advanced. The urethra may then be viewed through an endoscope positioned in the lumen of the introducer sheath as the irrigation fluid circulation is continued. A unitary connector is detachably coupled to a proximal end of the elongated sleeve, and a fluid seal is disposed between the unitary connector and the proximal end of the elongated sleeve. The unitary connector is configured to connect the first and second channels to the inflow pump and the outflow pump, respectively.

12 Claims, 10 Drawing Sheets

(51) Int. Cl.
*A61B 17/34* (2006.01)
*A61M 1/00* (2006.01)
*A61B 18/14* (2006.01)
*A61B 1/307* (2006.01)
*A61B 17/00* (2006.01)
*A61B 18/00* (2006.01)

(52) U.S. Cl.
CPC ........ *A61B 18/149* (2013.01); *A61B 18/1485* (2013.01); *A61M 1/0058* (2013.01); *A61M 25/01* (2013.01); *A61B 2017/0046* (2013.01); *A61B 2017/00274* (2013.01); *A61B 2017/00477* (2013.01); *A61B 2017/345* (2013.01); *A61B 2017/3445* (2013.01); *A61B 2018/00208* (2013.01); *A61B 2018/00982* (2013.01); *A61B 2217/005* (2013.01); *A61B 2217/007* (2013.01); *A61B 2218/002* (2013.01); *A61B 2218/007* (2013.01)

(58) Field of Classification Search
CPC .... A61B 2018/00982; A61B 2018/144; A61B 17/42; A61B 17/3205; A61B 17/320016; A61B 2017/320028; A61B 17/32002; A61B 10/0233; A61B 10/0241; A61B 2018/1475; A61B 18/1482; A61B 2018/1472; A61B 2218/001; A61B 2017/00274; A61B 2017/00353; A61B 2017/0046; A61B 2017/00464; A61B 2017/00469; A61B 2017/00473; A61B 2017/00477; A61M 1/0058; A61M 25/01; A61M 1/0066

USPC ........ 600/114, 153, 156, 109, 112, 121–123, 600/135, 152, 158–160, 172, 174, 105; 606/119, 167, 170, 171, 180

See application file for complete search history.

(56) References Cited

U.S. PATENT DOCUMENTS

| | | | |
|---|---|---|---|
| 9,028,398 B2* | 5/2015 | Kumar | ............... A61B 1/00068 600/105 |
| 2005/0234298 A1* | 10/2005 | Kucklick | ........... A61B 1/00135 600/156 |
| 2007/0213704 A1 | 9/2007 | Truckai et al. | |
| 2007/0270647 A1* | 11/2007 | Nahen | .................... A61B 1/015 600/131 |
| 2008/0262308 A1* | 10/2008 | Prestezog | .............. A61B 1/015 600/123 |
| 2009/0270849 A1 | 10/2009 | Truckai et al. | |
| 2010/0305565 A1 | 12/2010 | Truckai et al. | |
| 2013/0090642 A1 | 4/2013 | Shadduck et al. | |
| 2014/0336643 A1 | 11/2014 | Orczy-Timko et al. | |
| 2016/0143512 A1* | 5/2016 | Cheng | ................ A61B 1/00128 600/123 |

* cited by examiner

SURGICAL DEVICE AND METHOD OF USE

CROSS-REFERENCE TO RELATED APPLICATIONS

This application claims the benefit of Provisional No. 62/242,519, filed Oct. 16, 2015, the entire content of which is incorporated herein by reference.

BACKGROUND OF THE INVENTION

Field of the Invention

The present invention relates to devices and methods for resecting and removing tissue from the interior of a patient's body, for example in a transurethral resection of prostate tissue to treat benign prostatic hyperplasia.

Electrosurgical cutting devices often comprise a shaft or sleeve having a tissue extraction lumen with one or more radio frequency (RF) cutting blades arranged to resect tissue which may then be drawn into the extraction lumen, often via vacuum assistance through a cutting window. Most such electrosurgical tissue cutting devices rely on manually engaging the cutting window against the target tissue to be resected.

For resection of remote tissue sites, such as the prostate, it is usually desireable to introduce the surgical cutter through a tubular introducer device. Which such tubular introducers can be advanced "blind," i.e. without direct optical visualization, it is frequently desirable to prove such direct visualization. For example, it would be desirable to use an endoscope to observe the urethra while transurethrally advancing an introducer sheath for subsequent resection of the prostrate. Once the introducer sheath is in place, however, it will be necessary to advance the cutter through the introducer sheath which can require that fluid recirculation pumps be disconnected from the introducer sheath and reconnected to the surgical cutter. Such an exchange can be time consuming, and often the surgical cutter will require a different pumps and/or or pump interface than does the introducer sheath.

For these reasons, it would be desirable to provide improved urethral and other introducers for use with electrosurgical cutting tools. It would be particularly desirable if the introducer sheaths were easily connectable to and disconnectable from a pumping and control system that can be used both for initial advancement of the introducer sheath and for subsequent connection of the surgical cutter or other surgical tool. At least some of these objectives will be met by the inventions described below.

Related patents and published applications include U.S. Pat. Nos. 8,221,404; 7,744,595; U.S. Pat. Publ. 2014/0336643; U.S. Pat. Publ. 2010/0305565; U.S. Pat. Publ. 2007/0213704; U.S. Pat. Publ. 2009/0270849; and U.S. Pat. Publ. 2013/0090642.

SUMMARY OF THE INVENTION

In a first aspect of the present invention, an optical introducer system comprises an elongated sleeve having an endoscope-receiving passageway and first and second channels extending therethrough. A unitary connector is detachably coupled to a proximal end of the elongated sleeve, and a fluid seal is disposed between the unitary connector and the proximal end of the elongated sleeve. The unitary connector is configured to connect the first and second channels to an inflow pump and an outflow pump, respectively.

In specific embodiments, the unitary connector may include a first isolated flow channels for flowing irrigation fluid from the inflow pump to the elongated sleeve and a second isolated flow channel for removing irrigation fluid from the elongated sleeve. The unitary connecter typically further comprises a body and a detachable conduit having one end configured to be coupled to the inflow pump and the outflow pump and another end configured to be removably attached to the body. A third channel may be provided in the elongated sleeve for fluidic communication with a pressure sensor, and the optical introducer system may further comprise a controller operatively coupled to the inflow pump, the outflow pump and the pressure sensor. The controller may also house the inflow pump and the outflow pump, and the conduit may be extendable from the controller to the body, where the conduit includes a third isolated channel for connecting the third channel in the elongated sleeve to the controller. The elongated sleeve may have a fourth channel configured to removably receive a shaft of a diagnostic or therapeutic tool. The fourth channel is typically configured to removably receive a tissue resecting device, where the tissue resecting device may be a mechanical resecting device, an electrosurgical resecting device, or other device. The elongated sleeve may have a proximal end adapted for coupling to a tissue resecting device and may be dimensioned for trans-urethral access to a patient's prostate and/or bladder. The first, second and third channels typically have a mean diameter of at least 1 mm.

In a first aspect of the present invention, a method for positioning an introducer sheath into a patient's urethra comprises advancing a distal end of the introducer sheath into the patient's urethra, flowing an irrigation fluid through a lumen and out a distal end of the introducer sheath into the urethra, and simultaneously removing the irrigation fluid from the urethra through the distal end and lumen of the introducer sheath to establish a circulation of the irrigation fluid in the urethra as the introducer sheath is advanced. The urethra may then be viewed through an endoscope positioned in the lumen of the introducer sheath as the irrigation fluid circulation is continued.

In specific embodiments, the irrigation fluid may be pumped with at least one pump to flow into the urethra and to simultaneously removing the irrigation fluid from the urethra. More typically, however, the irrigation fluid will be pumped into the urethra with an inflow pump and will be aspirated from the urethra with an outflow pump. The inflow pump typically communicates with an inflow channel in the sheath and the outflow pump typically communicates with an outflow channel in the sheath. The inflow and outflow pumps may be connected to the introducer sheath by a unitary connector which is detachably attached to a proximal end of the introducer sheath. The methods may further comprise detaching the unitary connector from the introducer sheath and attaching a resection device to a proximal end of the introducer sheath. The resection device is typically inserted through the introducer sheath while said sheath remains in the patient's urethra. Fluid pressure in the urethra may be measured with a pressure sensor operatively coupled to the sheath where the pressure sensor may communicate through an independent flow channel in the sheath. Typically, the inflow pump and outflow pump are controlled to control pressure in the urethra.

DETAILED DESCRIPTION OF THE INVENTION

Figure 1:
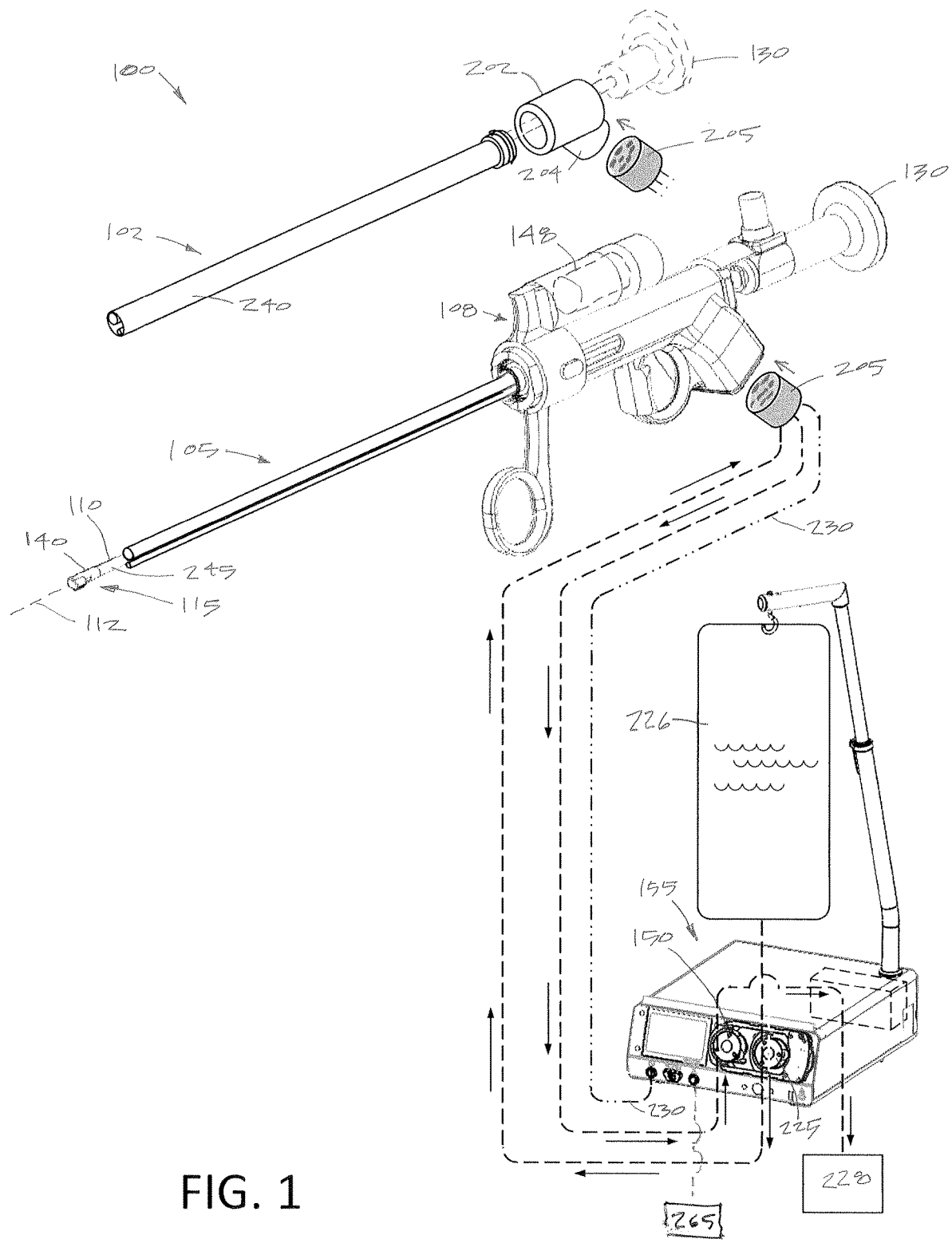
FIG. 1 is a view of a tissue resecting device and a block diagram of systems and operating components corresponding to the invention.

FIG. 1 illustrates an electrosurgical tissue resecting system 100 for use in urological procedures to resect tissue that includes an introducer sleeve or sheath 102 and a hand-held single-use tissue resecting device or probe 105. The resecting device 105 has a handle portion 108 that is coupled to an elongated shaft or extension portion 110 that has an outer diameter ranging from about 2 mm to 7 mm, and in one variation is 5 mm in diameter. The shaft 110 extends about longitudinal axis 112 to a working end 115 that is radially asymmetric relative the shaft 110 and its axis 112 as further described below. In one variation, the device is adapted for performing a TURP procedure (transurethral resection of prostate) or a bladder tumor resection procedure and thus the shaft portion 110 extends about axis 112 with a length suitable for introducing in a transurethral approach to reach the targeted prostate tissue or bladder tissue.

As will be described below and shown in FIG. 1, the resecting device 105 is adapted for introduction through the introducer sleeve 102. Such an introducer sleeve 102 is adapted to receive a commercially available endoscope 130 as can be understood from FIG. 1.

Figure 2:
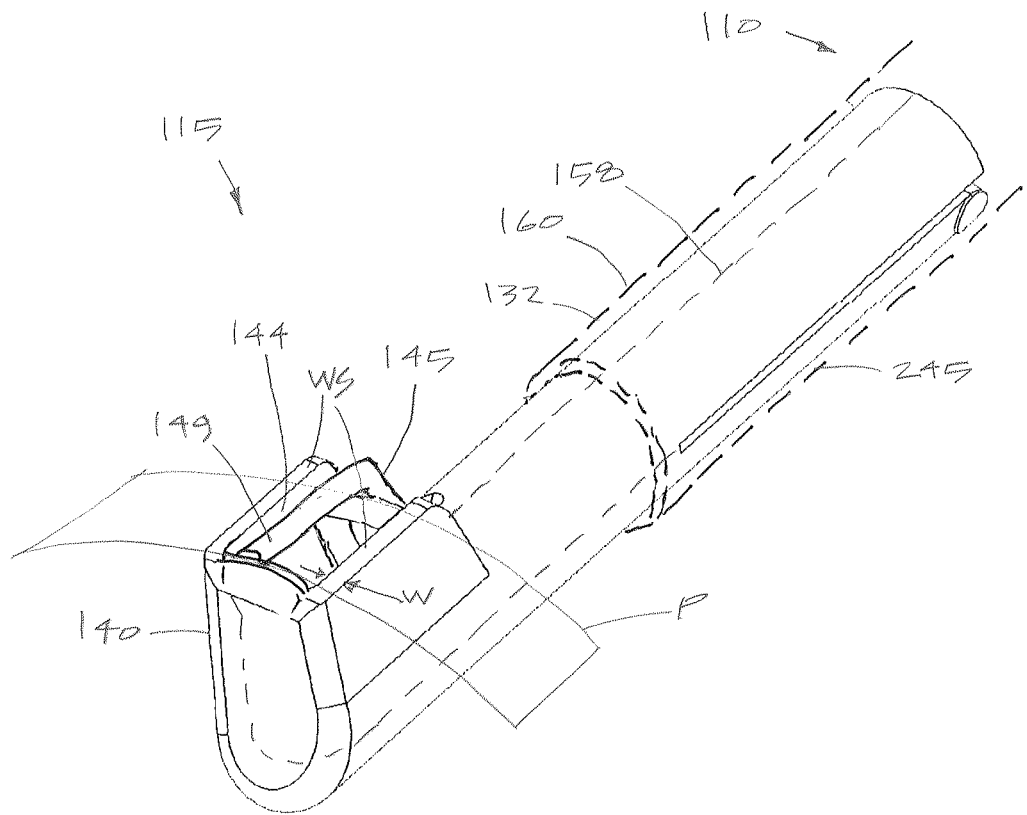
FIG. 2 is a perspective view of the working end of the resecting device of FIG. 1 showing an asymmetric ceramic housing and moving electrode that is adapted to sweep across a tissue-receiving window.
Figure 3:
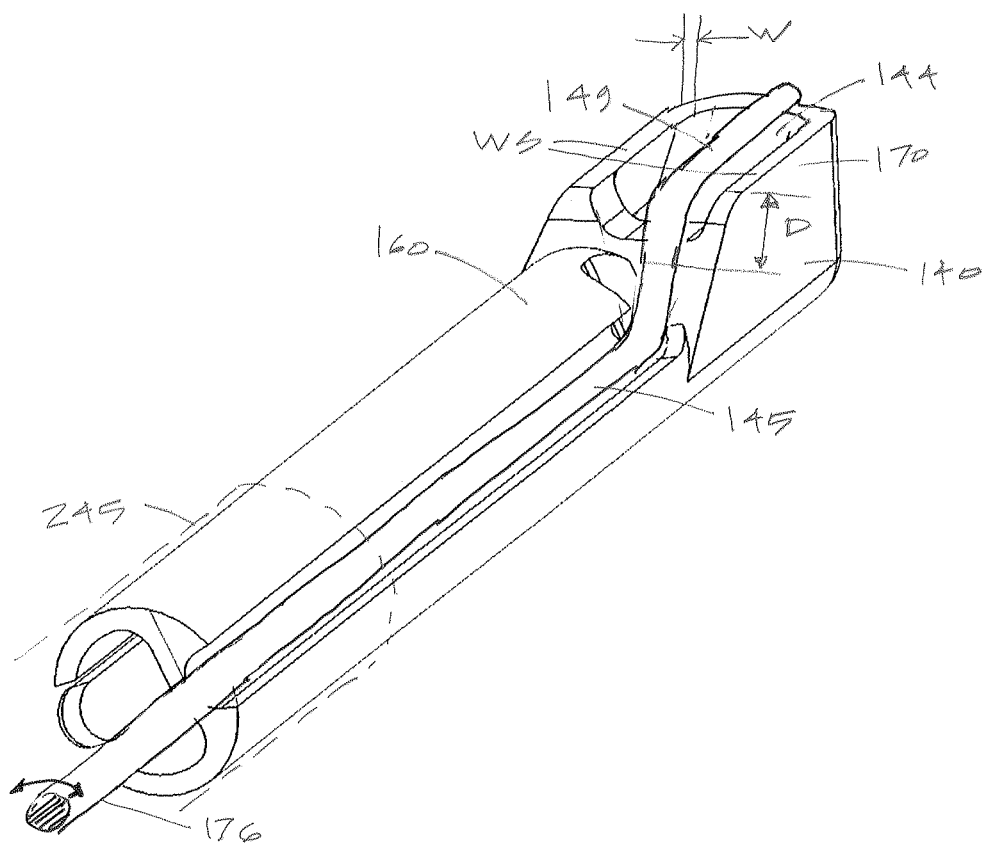
FIG. 3 is another perspective view of the working end of FIG. 2 from a different angle.

Referring to FIGS. 1-3, in general, it can be seen the resecting device 105 has an elongated shaft 110 that extends to a distal shaft portion 132 that is coupled to an offset resecting housing 140 that has an offset tissue-receiving window 144. A moveable electrode 145 is adapted to be driven by a motor drive unit 148 in handle 108 (see FIG. 1) so that the longitudinal portion 149 of the electrode 145 sweeps across the window 144 from side to side to electrosurgically resect tissue that is captured in the window 144. The targeted tissue can be suctioned into and captured in window 144 by means of a negative pressure source or outflow pump 150 in controller 155 that communicates with a tissue extraction channel 158 extending through the device 105 and terminating in the window 144.

Figure 4A:
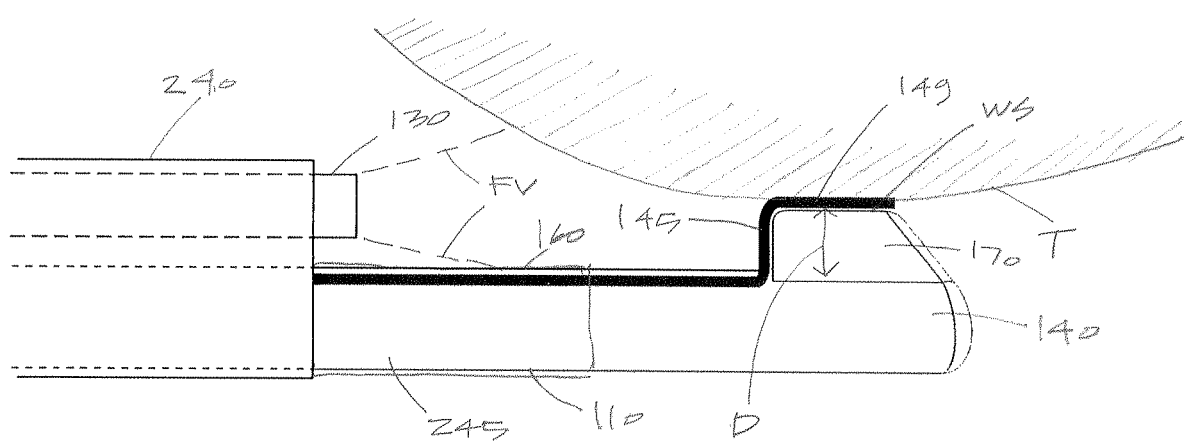
FIG. 4A is a schematic view of the working end of FIGS. 2-3 interfacing with tissue targeted for resection under endoscopic vision.

More in particular, referring to FIGS. 2 and 3, the configuration of the offset housing 140 is adapted to perform multiple functions. First, the offset housing 140 positions the window surface WS (within curved plane P indicated in FIG. 2) outwardly from the outer surface 160 of shaft 110 which then allows the window surface WS to be fully visible through a endoscope 130 or other viewing means that would be introduced parallel to the device shaft 110 (see FIG. 4A). For example, FIG. 4A is a schematic view of the working end 115 with working surface WS in contact with targeted tissue T. As can be seen in FIG. 4A, the endoscope 130 is positioned with the field of view FV directly aligned with the working surface WS thus allowing optimal viewing of the tissue resection process.

Figure 4B:
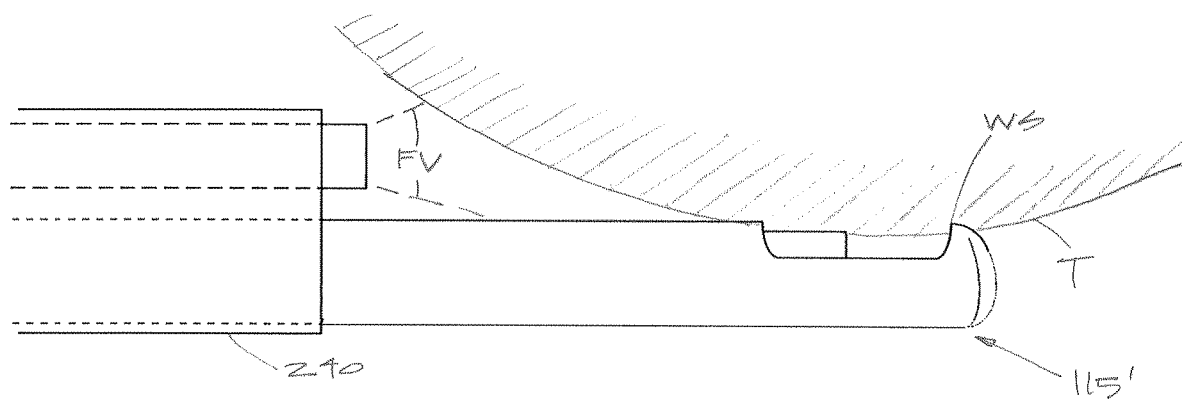
FIG. 4B is a schematic view of a working end of a prior art tubular cutting device used in a hypothetical resection procedure.

In contrast, FIG. 4B shows a working end 115' of a conventional dual sleeve tubular cutter having a window surface WS' which when pressed against an organ prevents endoscopic vision of the interface between the tubular cutting edge and the tissue T during a resection procedure.

Figure 5:
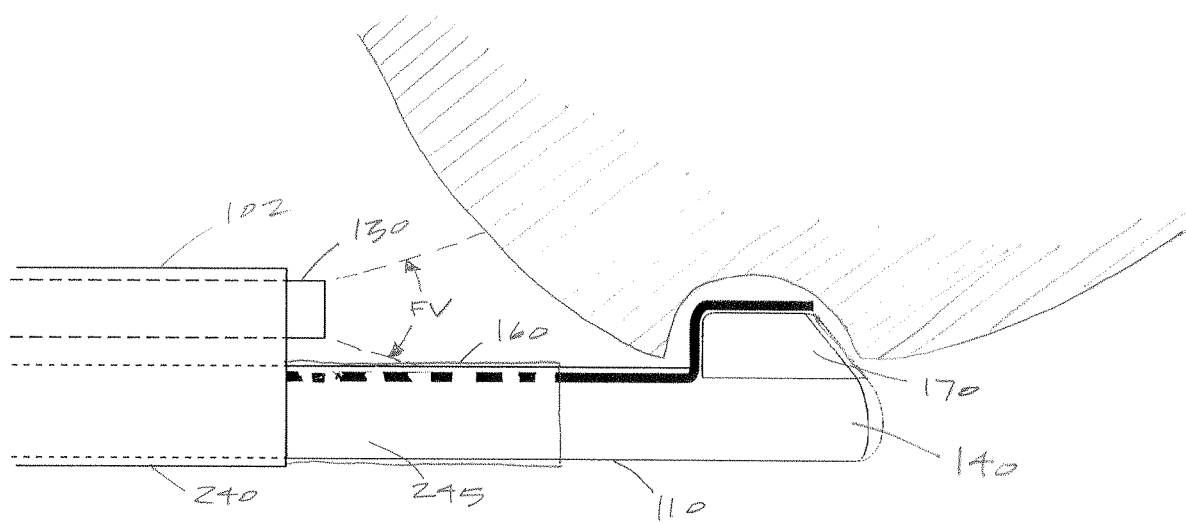
FIG. 5 is another schematic view of the working end of FIGS. 2-3 being used to resect targeted tissue to a significant depth from the organ surface.

Second, the offset housing 140 is adapted for resecting tissue to a greater depth in a localized region of an organ, rather than resecting surface tissues over a broad area. More in particular as shown in FIG. 5, the offset portion 170 of housing 140 can be pushed into tissue perpendicular to axis 112 of the probe shaft 110. Thus, as shown in FIG. 5, the offset housing 140 can be used to resect tissue deep into in a localized region that would not be possible with a resecting device having the configuration shown in FIG. 4B.

FIGS. 2 and 3 illustrate the asymmetric or offset dielectric housing 140 that can comprise a ceramic material such as zirconium oxide, aluminum oxide or similar materials as is known in the art. In FIGS. 2-3, it can be seen that window surface WS is offset from the shaft surface 160 by a predetermined dimension D which can be from 2 mm to 8 mm and in one embodiment comprises a 5 mm offset.

As can be further be seen in FIGS. 2-3, the width W of the window surface WS around at least portions of the perimeter of the window 144 is a limited dimension, for example less than 3 mm, or less than 2 mm or less than 1 mm. which allows the offset portion 170 of housing 140 to be pushed into tissue perpendicular to the device axis 112 as the electrode 145 sweeps across the window 144.

Referring to FIGS. 2-3, one variation of resecting device 105 has an electrode 145 that can be tungsten or stainless steel wire that with electrode portion 149 adapted to sweep across the window 144 at any suitable rate, for example from 1 Hz to 500 Hz. In FIG. 3, it can be understood that the electrode 145 has an elongated proximal shaft portion 176 that extends into handle 108 of the device (FIG. 1). The proximal end of electrode 145 is operatively coupled to a motor drive unit 148 and a suitable mechanism or controller is provided to rotate the elongated electrode shaft portion 176 in an arc to resect tissue.

As can be understood from FIGS. 2-3, the electrode portion 149 moves back and forth akin to a windshield wiper across window 144 in the offset housing 140. A number of mechanisms can be used to effectuate the desired movements of the electrode, or the motor drive 148 simply can be controlled by software to move in intermittent clockwise and counter-clockwise directions. In one variation, the elongated proximal portion 176 of the electrode 145 will twist over its length and thus the motor drive 148 can be adapted to rotate the electrode shaft in an arc with radial angle which is greater than the window's comparable radial angle or arc. Thus, the electrode portion 149 can be expected to move back and forth entirely across the window even when meeting some tissue resistance by compensating for some twisting that is allowed in the proximal electrode shaft portion 176. In one variation, the motor drive unit can be adapted to over-rotate the electrode shaft portion 176 at its proximal end by a selected amount which can be from 10° radial motion to 90° radial motion to compensate for twisting of the electrode shaft portion to insure that electrode portion 149 sweeps entirely across the surface of window 144.

Figure 6:
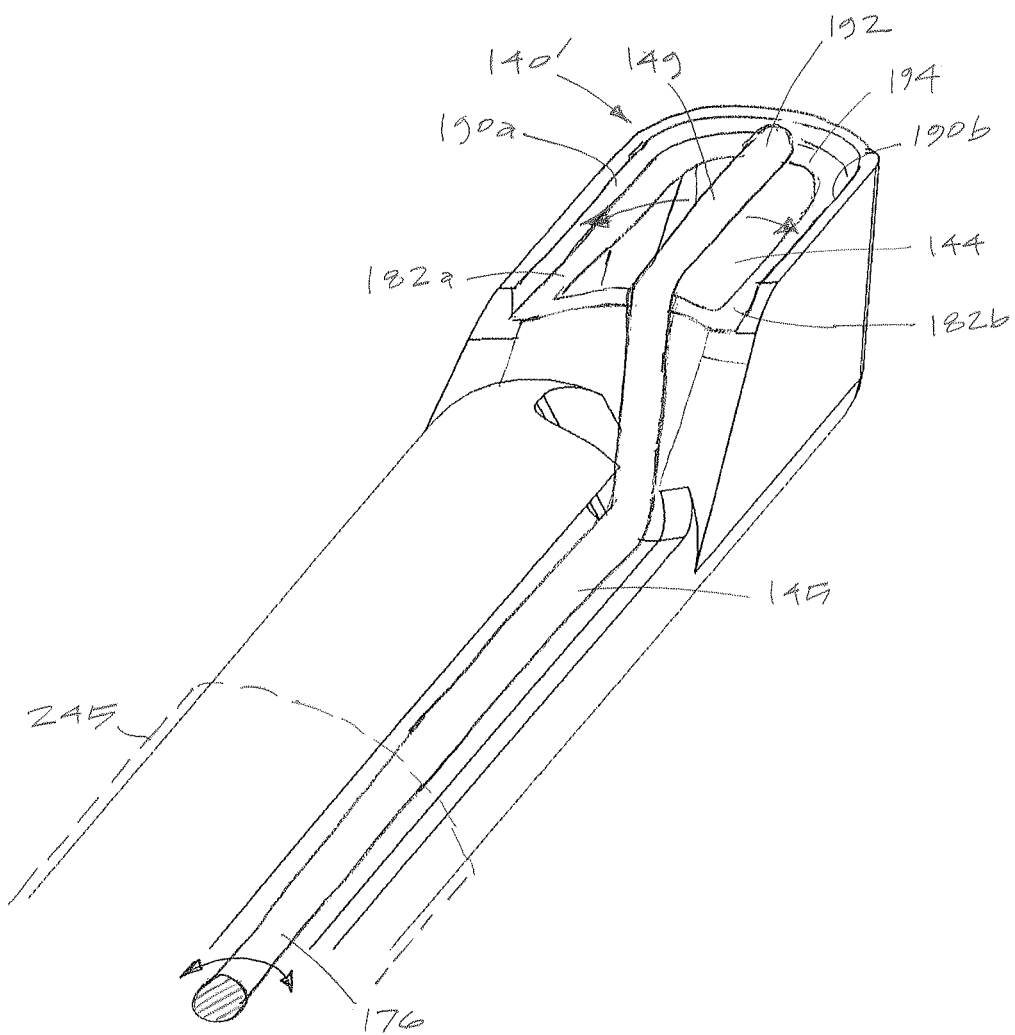
FIG. 6 is a perspective view of a distal dielectric housing of a working end similar to that of FIGS. 2-3 showing window sides with ledges for receiving the electrode at the ends of its movement in a sweeping arc.

In general, the window 144 in housing 140 can be configured to have a radial arc relative to the electrode shaft 176 ranging between 30° and 180°. In one variation of housing 140' shown in FIG. 6, it can be seen that the electrode portion 149 has a range of motion that extends across the radial dimension of the window 144 to ensure that any tissue captured in the window is resected as the electrode portion 149 passes the window edges 182a and 182b to function like a shear or in a scissor-like manner. The electrode portion 149 moves over ledges 186a and 186b on either side of the housing 140' and can bump into surfaces 190a and 190b. By bumping into the surfaces 190a and 190b, any over rotation in the electrode shaft 176 to accommodate twisting as described above can limit the rotation of the electrode portion in the housing 140'. Further, in FIG. 6, it can be seen that the distal tip 192 of electrode portion 149 extends distally beyond window 144 and onto distal ledge 194 in the housing 140' to ensure tissue is resected by the electrode in the distal window region.

Now turning back to FIG. 1, it can be understood that the resecting device 105 and endoscope 130 can be used with introducer sleeve assembly or sheath 102. As shown in FIG. 1, the introducer assembly 102 has a proximal handle body 202 with a connector 204 that is adapted to couple to connector member 205. The connector 205 is adapted to couple a conduit 206 to controller 155 and provide within a single cable 230 the following: (i) a first lumen communicating with the fluid outflow pump 150, (ii) a second lumen communicating with a fluid inflow pump 225, and (iii) a third lumen communicating with a pressure sensor positioned in the controller 155 or in or near the connector 205. As can be seen in FIG. 1, the introducer sleeve 102 can also accommodate an endoscope 130. Thus, the introducer sleeve 120 can be assembled with the endoscope 130 (and without the resection device 105) and coupled by connector 205 to the controller 155 to provide an inflow of irrigation fluid from fluid source 226, and outflow of irrigation fluid to collection reservoir 228 together with pressure sensing to allow the assembly to be used in a diagnostic procedure prior to a tissue resection procedure. In other words, the introducer sleeve 102 can function as a 'continuous flow' optical introducer for use in trans-urethral access to a targeted sire in the prostate or bladder.

After the introducer sleeve assembly 102 is used for an initial diagnostic procedure, the endoscope 130 can be removed from the assembly 102 and connector 205 can be disconnected from handle body 205. Thereafter, the sleeve portion 240 (see FIG. 1) of introducer assembly 102 can be detached from proximal handle body 204 with the sleeve portion 240 remaining in the patient. Next, the endoscope 130 and connector 205 can be assembled with the resecting device 105 and the physician can insert the resecting device 105 through the sleeve portion 240 remaining in the patient to access the targeted site. The resecting device 105 and sleeve portion 204 in combination then provide lumens as described above for fluid inflows, fluid outflows and direct pressure sensing through lumens in connector 205.

Figure 7A:
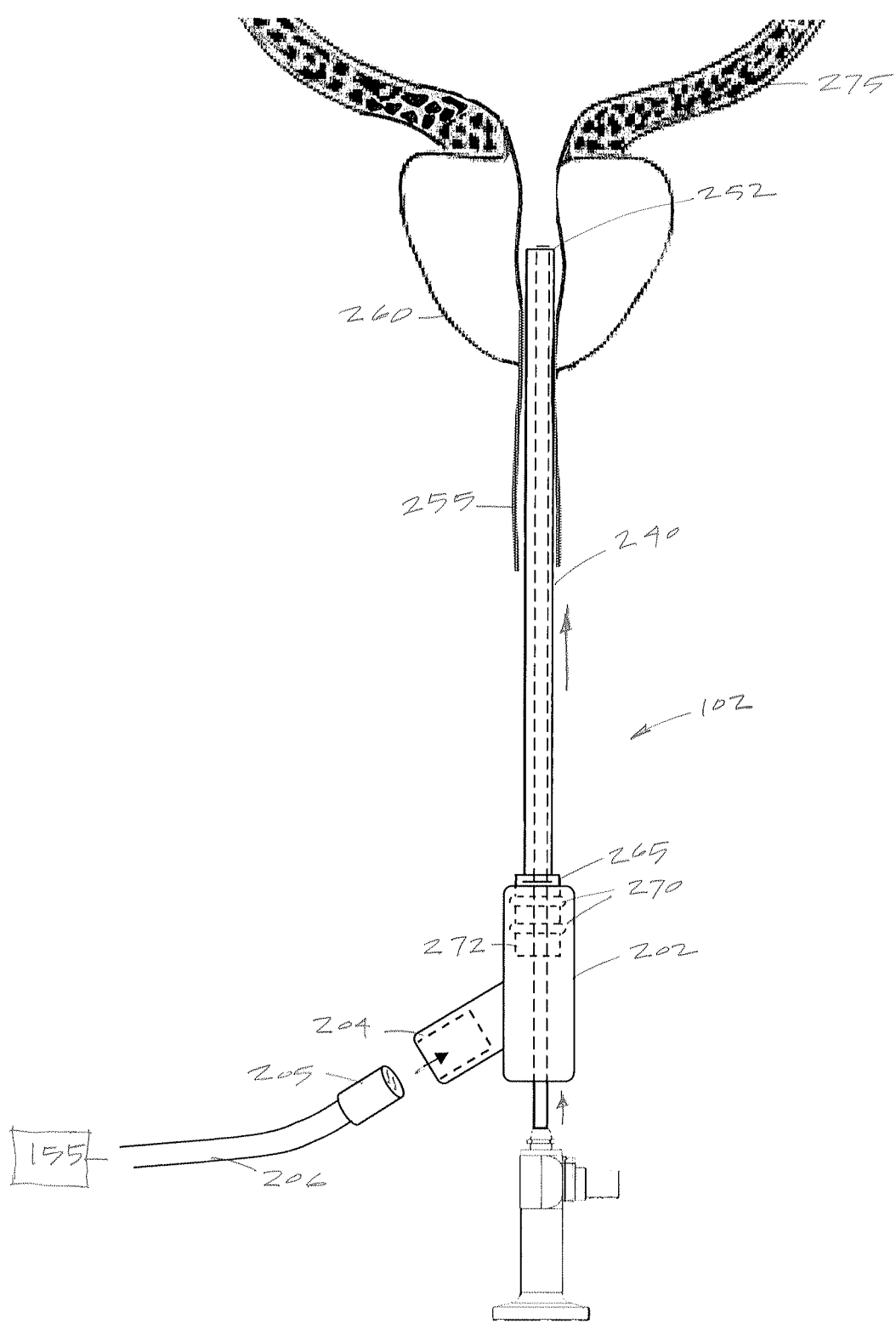
FIG. 7A is a schematic view of a method of the invention wherein an endoscope is inserted into the introducer assembly and a conduit is coupled to the introducer assembly to couple flow channels therein to a controller with an inflow pump and an outflow pump, wherein FIG. 7A then illustrates the step of introducing the introducer assembly into a patient's urethra to access the prostate under endoscopic vision and continuous flow irrigation.
Figure 7B:
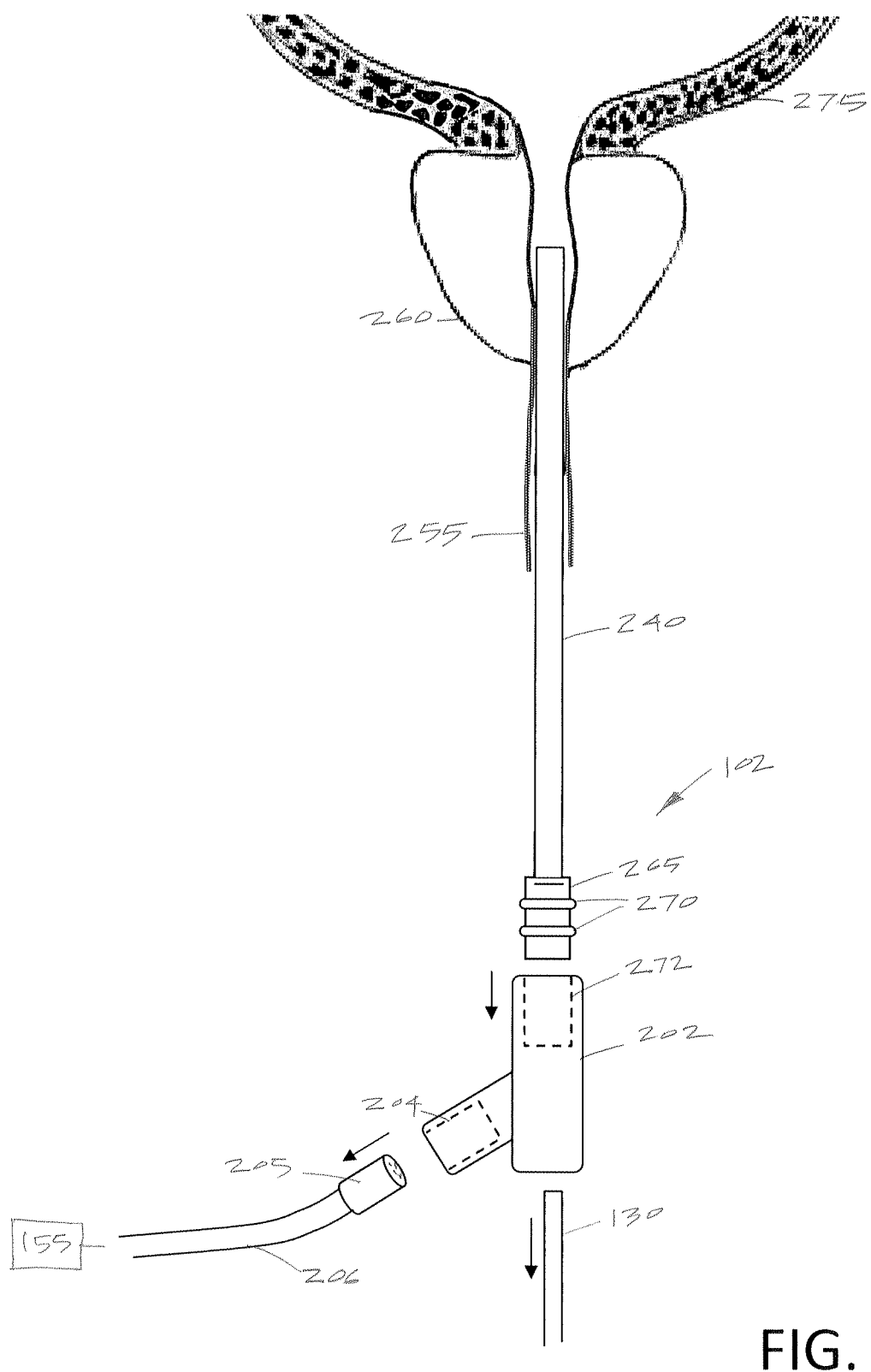
FIG. 7B illustrates a subsequent step wherein the endoscope is withdrawn from the introducer assembly and then handle of the introducer assembly is detached from a sleeve portion and the sleeve portion remains in place to access a site in the patient's prostate.
Figure 7C:
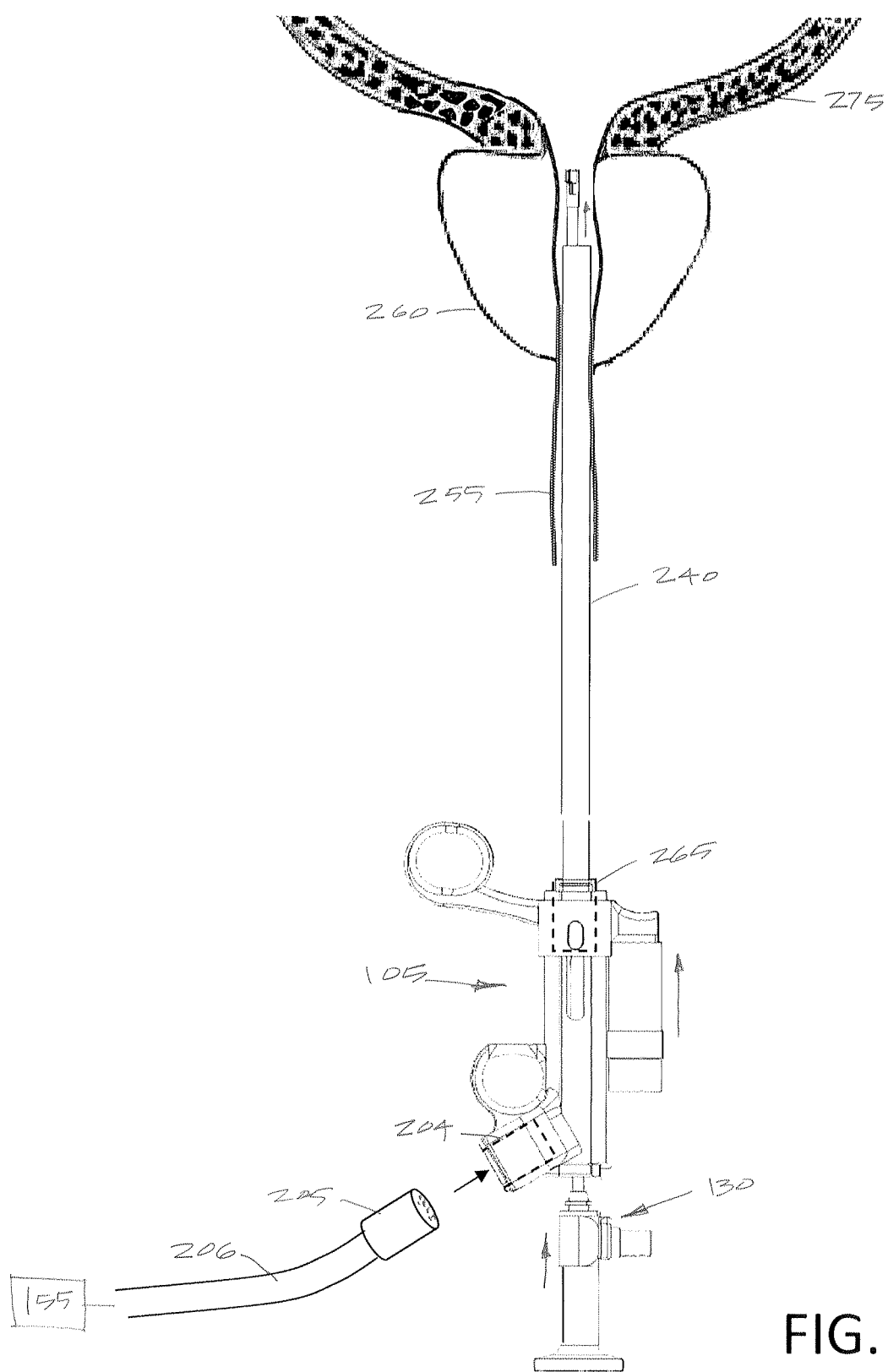
FIG. 7C illustrates a further subsequent step wherein the endoscope inserted into the resecting device, which then is inserted into sleeve portion remaining in the patient to access the treatment site in the prostate or bladder, and the conduit can be coupled to the resecting device either before or after its insertion through the sleeve portion.

The method of using the introducer assembly is shown in more detail in FIGS. 7A-7C. More in particular, FIG. 7A illustrates the endoscope 130 inserted into the introducer assembly 102 and conduit 206 being coupled to the introducer assembly 102 to couple the inflow and outflow channels to controller 155 to provide a continuous inflow and outflow at the distal end 252 of sleeve portion 240. FIG. 7A further illustrates the step of introducing the introducer assembly 102 into a patient's urethra 255 to access the prostate 260 or bladder 275 under endoscopic vision and continuous flow irrigation.

FIG. 7B illustrates a subsequent step wherein the endoscope 130 is withdrawn from the introducer assembly 102 and then the handle 202 of introducer assembly 102 is detached from a sleeve portion 240 and the sleeve portion 240 remains in place to access a site in the patient's prostate 260. As can be seen in FIG. 7B, the proximal end 264 of sleeve portion 240 is configured with a body 265 and at least one seal member 270 such as an o-ring to provide a fluidic seal when mated with receiving connector portion 272 in handle 202.

FIG. 7C illustrates a further subsequent step wherein the endoscope 130 inserted into the resecting device 105, and thereafter the assembly of the resecting device 105 and endoscope are inserted into sleeve portion 240 remaining in the patient to access the treatment site in the prostate 206 or bladder 275. The proximal body 265 of sleeve portion with it seal member 270 then mates with a receiving channel in the resecting device handle to provide a fluidic seal. The conduit 206 can be coupled to the resecting device 105 which has a receiving connector 204 similar to that of introducer assembly handle 202. In use, the system then provides for continuous flow irrigation and extraction of fluid and tissue chips through the resecting device.

In another variation, the introducer sleeve assembly 102 can include a removable blunt tip obturator that can assist in atraumatic insertion into a patient's urethra.

Referring to FIGS. 2-3, one variation of the resecting device as described above has an electrode 145 with a resecting portion 149 that moves radially in an arc relative to axis 112 and a distal window 144. Another variation can provide an electrode 145 that reciprocates axially to move across the window 144 and would have similar effectiveness.

Referring back to FIG. 1, the electrode 145 comprises a first polarity electrode or active electrode and the shaft portion indicated that 245 comprises the return electrode.

Referring to FIG. 1, the resecting device 105 can be actuated by moveable finger grip 260 which is adapted to be squeezed toward fixed finger grip 262 to thus move the working end 115 and window surface WS axially back and forth to resect tissue. The physician can activate the electrosurgical function with a foot switch 265 (FIG. 1) and then reciprocate the working end 115 back and forth from about 5 mm to 25 mm to resect tissue in a path. At the same time, the physician can slightly rotate the shaft of the resecting device 105 so that the window surface WS engages a wider path in the targeted tissue surface.

In typical use, the physician would stabilize the sleeve portion 240 and endoscope 130, and then reciprocate and slightly rotate the resecting device 105 during a tissue resection procedure. During such a procedure, the physician can also slightly rotate the sleeve 240 and endoscope 130 to optimize viewing of the targeted tissue.

What is claimed is:

1. A medical method for positioning an introducer sheath and a resection device in a patient's urethra, said method comprising:
   positioning an endoscope through a lumen of the introducer sheath;
   advancing a distal end of the introducer sheath into the patient's urethra;
   flowing an irrigation fluid into the urethra through an inflow channel that terminates at the distal end of the introducer sheath and simultaneously removing the irrigation fluid from the urethra through an outflow channel that terminates at the distal end of the introducer sheath to establish a circulation of the irrigation fluid in the urethra as the introducer sheath is advanced into the patient's urethra;
   viewing the urethra through the endoscope positioned in the lumen of the introducer sheath as the introducer sheath is advanced into the patient's urethra and the irrigation fluid circulation is continued;
   removing the endoscope from the lumen of the introducer sheath after the distal end of the introducer sheath has reached a target tissue;
   inserting the resection device into the lumen of the sheath;
   positioning the endoscope through the resection device;
   continuously circulating irrigation fluid; and
   extracting fluid and tissue chips through the resecting device.

2. The medical method of claim 1, wherein flowing the irrigation fluid into the urethra and simultaneously removing the irrigation fluid from the urethra comprises pumping the irrigation fluid with at least one pump.

3. The medical method of claim 2, wherein flowing the irrigation fluid into the urethra and simultaneously removing the irrigation fluid from the urethra comprises pumping the irrigation fluid into the urethra with an inflow pump and aspirating irrigation fluid from the urethra with an outflow pump.

4. The medical method of claim 3, wherein the inflow pump communicates with the inflow channel in the sheath and the outflow pump communicates with the outflow channel in the sheath.

5. The medical method of claim 4, wherein the inflow and outflow pumps are connected to the introducer sheath by a unitary connector which is detachably attached to a proximal end of the introducer sheath while the introducer sheath is advanced into the patient's urethra and the irrigation fluid circulation is continued.

6. The medical method of claim 5, further comprising detaching the unitary connector from the introducer sheath and attaching the resection device to the proximal end of the introducer sheath.

7. The medical method of claim 6, wherein attaching the resection device comprises inserting an elongated shaft of the resection device through the lumen of the introducer sheath while said introducer sheath remains in the patient's urethra.

8. The medical method of claim 7, further comprising attaching the unitary connector to a handle of the resection device.

9. The medical method of claim 8, further comprising flowing the irrigation fluid through the unitary connector connected to the handle of the resection device.

10. The medical method of claim 3, further comprising measuring fluid pressure in the urethra with a pressure sensor operatively coupled to the sheath.

11. The medical method of claim 10, wherein the pressure sensor communicates with an independent flow channel in the sheath.

12. The medical method of claim 3, further comprising controlling the inflow pump and the outflow pump to control pressure in the urethra.

* * * * *